United States Patent [19]

Bickford et al.

[11] Patent Number: 4,779,163

[45] Date of Patent: Oct. 18, 1988

[54] METHOD AND APPARATUS FOR CONTROLLING ELECTROSTATIC CHARGES IN FLUIDIZED BEDS

[75] Inventors: Karin Bickford, Plainsboro; Joseph E. Japka, Cherry Hill; Robert B. Roaper, Martinsville, all of N.J.

[73] Assignee: Procedyne Corp., New Brunswick, N.J.

[21] Appl. No.: 586,021

[22] Filed: Mar. 5, 1984

Related U.S. Application Data

[63] Continuation-in-part of Ser. No. 401,090, Jul. 23, 1982.

[51] Int. Cl.$^4$ .......................... H05F 3/02; F26B 17/10
[52] U.S. Cl. ...................... 361/212; 432/27; 324/454; 374/45; 374/57; 219/359
[58] Field of Search ............... 361/212, 215, 220, 226; 219/359, 360, 369, 388, 390, 399, 406, 407, 430, 439; 34/10, 57 A, 57 C; 165/104.16; 432/15, 18, 27, 58, 261; 373/109, 110; 374/45, 57; 324/158 F

[56] References Cited

U.S. PATENT DOCUMENTS

| | | | |
|---|---|---|---|
| 3,117,027 | 1/1964 | Lindlof et al. | 361/212 X |
| 3,749,805 | 7/1973 | Seelandt et al. | 219/359 X |
| 3,921,307 | 11/1975 | Marek et al. | 165/104.16 X |
| 4,275,353 | 6/1981 | Yang et al. | 324/454 |
| 4,303,961 | 12/1981 | Wydeven et al. | 361/226 X |
| 4,457,788 | 7/1984 | Staffin et al. | 432/27 X |
| 4,519,718 | 5/1985 | Staffin et al. | 374/45 |

FOREIGN PATENT DOCUMENTS

| | | | |
|---|---|---|---|
| 1473700 | 11/1969 | Fed. Rep. of Germany | 374/45 |
| 668107 | 6/1979 | U.S.S.R. | 361/215 |

Primary Examiner—L. T. Hix
Assistant Examiner—D. Rutledge
Attorney, Agent, or Firm—Kane, Dalsimer, Sullivan, Kurucz, Levy, Eisele and Richard

[57] ABSTRACT

A fluidized bed method and apparatus involving a grounded electrically conductive bed for controlling or eliminating electrostatic charges therein and high surface area charge dissipators.

15 Claims, 2 Drawing Sheets

METHOD AND APPARATUS FOR CONTROLLING ELECTROSTATIC CHARGES IN FLUIDIZED BEDS

This application is a continuation-in-part of co-pending application Ser. No. 401,090, filed on July 23, 1982.

FIELD OF THE INVENTION

The present invention is related to the field of static elimination and, more specifically, a method and apparatus for controlling and/or eliminating static charge in fluidized bed apparatus.

BACKGROUND OF THE INVENTION

A typical environment where static charge build-up in fluidized beds is a serious problem 6 in thermal testing of electronic components.

Generally, thermal shock testing involves subjecting an article to be tested, i.e., the workpiece to sudden heating and cooling by moving it to and from separate hot and cold environments. Thermal cycling tests involve changing the temperature of the thermal environment without moving the workpiece. These and related methods are hereinafter referred to collectively as Thermal Testing unless the context indicates otherwise.

Thermal Testing is extremely useful for evaluating the reliability of materials and devices because the thermal stresses created in such workpieces by sudden temperature changes tend to accelerate failures due to defects that would otherwise be undetectable until long after manufacture. For example, thermal testing is widely used in the electronics industry to detect defective semiconductor devices before they are installed in complex electronic systems where failure could result in expensive repairs and considerable down time.

A typical prior art device for conducting thermal testing would have an enclosed heat transfer medium provided with a heating means, e.g., electric resistance heaters, and/or a cooling means, e.g., gas expansion refrigeration. Specifically, a thermal cycling device would have a single heat transfer medium enclosure with both heating and cooling means, and a thermal shock device would have two such enclosures, one for cooling and the other for heating. In operation, the workpiece is simply submerged in the heat transfer media for a fixed period of time, and its temperature changes until it reaches or approaches thermal equilibrium with the heat transfer media.

The nature of the heat transfer media is a dominant factor in how fast the workpiece is heated or cooled, i.e., the rate at which the system approaches thermal equilibrium. Gaseous heat transfer media, usually air, have the advantage of being inexpensive and not contaminating the workpiece, thus avoiding subsequent cleaning operations before use. However, the heat transfer characteristics of gases are slow and hence they cannot change a workpiece's temperature fast enough to create sufficient thermal stresses to satisfactorily accelerate failures due to latent defects in the workpiece.

Liquids unlike gases, have very fast heat transfer characteristics and high heat capacities. Therefore, they make excellent heat transfer media for thermal testing. A workpiece submerged in liquid heat transfer media rapidly reaches or approaches thermal equilibrium with the system and sufficient thermal stresses to induce failure of the workpiece due to latent defects are attained. However, liquids also have drawbacks that make them undesirable for many thermal testing applications. Specifically, since suitable liquids that are stable at the temperatures contemplated for thermal testing, usually $-65°$ to $200°$ C., are usually very expensive and evaporation, dripping, and carryout losses are usually large, rendering the costs of such testing very high.

Volatility and toxicity of such liquids may also pose serious health hazards, fire hazards, and problems with governmental regulatory agencies as well. An additional problem with liquid heat transfer media in thermal testing devices is that the liquid may have to be cleaned from the workpiece to avoid problems in subsequent use, e.g., soldering.

Moreover, since few, if any liquids would be suitable for both extremely high and extremely low temperature applications some thermal shock systems using different high and low temperature liquid heat transfer media, i.e., liquid/liquid systems, are subject to cross-contamination caused by carryover when the workpiece is moved from one liquid to the other.

The disadvantages of liquid and gas thermal testing systems may be overcome by the use of fluidized solids is the place of gaseous or liquid heat transfer media.

One property of gas fluidized solids as a heat transfer medium that causes a problem in some thermal shock applications is that it tends to build up static charges due to the flow of fluidizing gas around the particles. In applications involving sophisticated electronic devices such as programmed chips, the static charges may affect the devices adversely.

SUMMARY OF THE INVENTION

It has been discovered that the above-mentioned disadvantages of fluidized bed systems associated with electrostatic charges may be obviated by using a fluidized bed media including at least some electrically conductive particles and providing electrical grounding for the bed media.

With the above and other incidental objects and advantages in view as will more fully appear in the specification, the invention intended to be protected by Letters Patent consists of the features of construction, the parts and combinations thereof, and the mode of operation as hereafter described or illustrated in the accompanying drawings, or their equivalents.

BRIEF DESCRIPTION OF THE DRAWINGS

Referring to the accompanying drawings wherein are shown some, but obviously not all, embodiments of the present invention.

DETAILED DESCRIPTION OF THE PREFERRED EMBODIMENTS

The fluidizing process causes a particulate solid bed to become an expanded mass that behaves like a boiling liquid having a zero angle of repose, seeking its own level and assuming the shape of the vessel it is contained in. This expanded mass state is accomplished by passing a gas upwardly through a particulate solid in an enclosure at sufficient velocity to suspend the particulate bed media so that it exhibits characteristics usually associated with low viscosity liquids. Preferred bed media exhibits no significant changes in physical properties over a wide range of temperatures and is not subject to melting point or boiling point limitations associated with liquids used at conventional thermal testing temperatures. Consequently, the same solid bed media may be useful for both heating and cooling operations and the cross contamination, discussed above, is totally eliminated. Any bed media adhering to a workpiece after testing is easily removed before subsequent use, by a light dusting.

There are many types and sizes of solids that can be used to form a gas-fluidized bed. It is an object of the present invention to provide solids which have a combination of physical properties, including electrical conductivity, to provide optimum Thermal Testing and prevent significant build up of the static electricity typically found in the fluidized beds after extended periods of operation at typical test temperatures. It is a further objective of this invention to provide an apparatus that dissipates static charges that are established in a fluidized bed to prevent a build up of static electricity therein.

EXAMPLE

Figure 1:
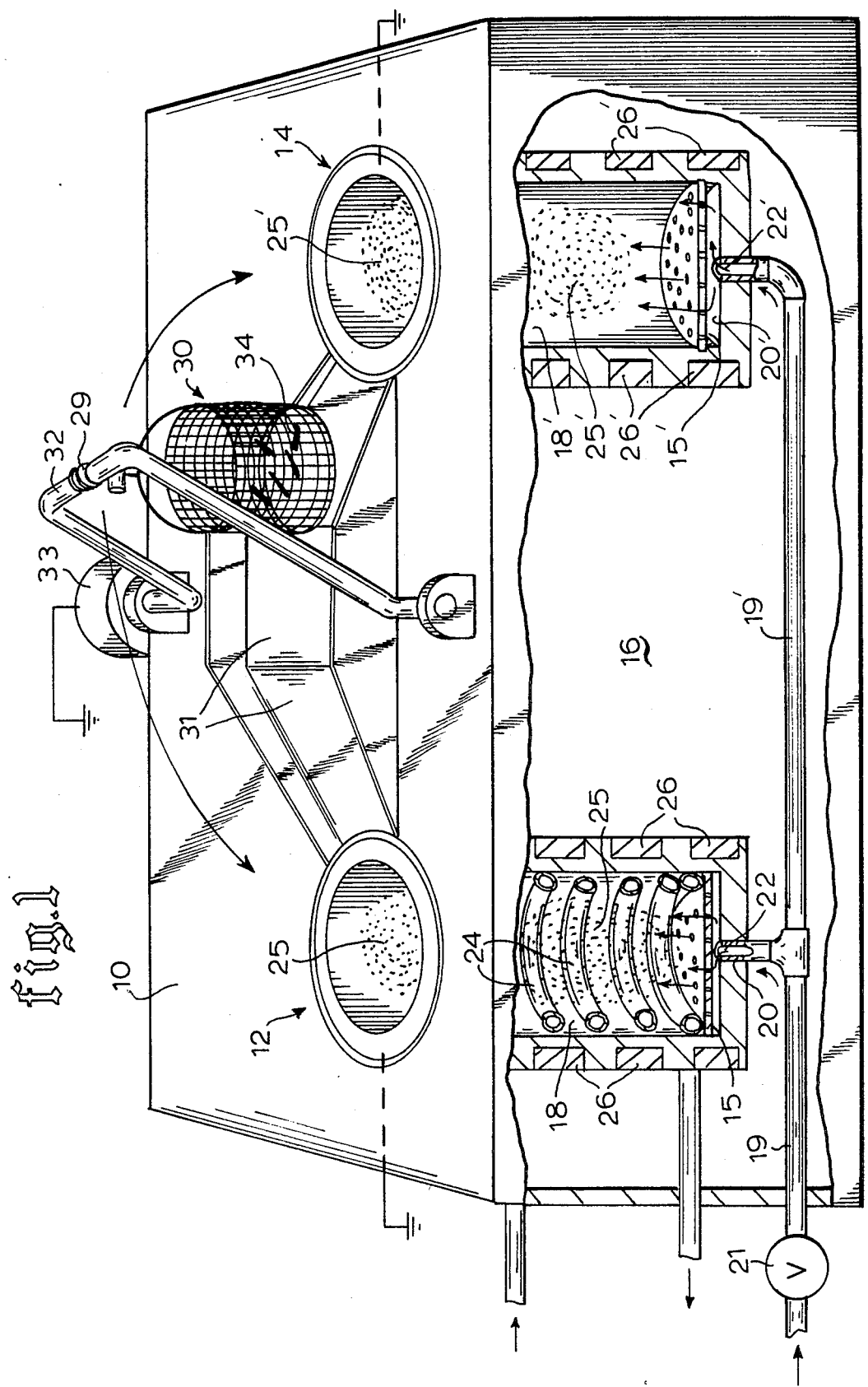
FIG. 1, is a partially cut away perspective view of a thermal testing device, utilizing a fluidized bed.

Thermal shock tester 10 illustrated in FIG. 1 is a typical fluidized bed system provided with two independent fluidized bed enclosures, 12 and 14, for performing cooling and heating operations, respectively. The enclosures 12 and 14 are separated by thermally insulating material 16.

The cooling enclosure 12 comprises a heat transfer portion 18 and a plenum 20 separated by distributor plate 15. Conduit 19, inlet 22 and valve 21 provide means for supplying a regulated flow of fluidizing gas to plenum 20. Heaters 26 disposed on the exterior walls of enclosure 12 and cooling coils 24 disposed within the enclosure 12 provide means for controlling the temperature within enclosure 12.

The heating enclosure 14 resembles cooling enclosure 12 in all respects except that no cooling coils 24 are provided therein. Parts of heting enclosure 14 corresponding to like parts of cooling enclosure 12 are indicated by the same reference numeral primed.

Workpiece support means, e.g., basket 30, supports one or more workpieces 34 to be heated and cooled in the enclosures 14 and 12. The basket 30 is suspended on a swivel connection 29 from the electromechanical transfer arm 32 so that it may be positioned in either enclosure by simple movement of the transfer arm by motor 33. The support means 30 may be made from electrically conductive material and connected to electrical ground to provide grounding for the expanded mass.

In operation, a fluidizing gas, e.g., nitrogen, air, or the like flows into the respective plenums 20 20' at a selected rate via valve 21, conduits 19, 19', and inlets 22 and 22'. The gas flows upwardly through distributor plates 15 and 15' entering heat transfer portions 18 and 18' of enclosures 12 and 14. The upwardly moving gas causes bed media particles, e.g., carbon or carbon plus aluminum or zirconium oxide or titanium oxide or titanium oxide with solute additions in particulate form of other metal oxide phases such as ferrites, chromia or alumina or the like or bed media substances with similar physical properties disposed therein to levitate producing expanded masses 25 and 25', that behave like a liquid. Accurate temperature adjustment of the expanded mass 25 in the cooling enclosure 12 is accomplished by circulating coolant through cooling coils 24 at maximum capacity and adjusting up to the desired temperature, e.g., $-65°$ with heaters 26. The temperature of the heating enclosure 14, e.g., 150° C. is controlled by heaters 26' alone.

A workpiece 34 to be tested is placed in basket 30 and the electromechanical means 33 and controlling arm 32 are then activated. The electromechanical means 33 automatically swings arm 32 from a rest position wherein the basket 30 suspended therefrom, as described above, is submerged in the cooled expanded mass 25 in enclosure 12 to a second rest position wherein the basket 30 is submerged in the heat expanded mass 25' in enclosure 14. The electromechanical means 33 is provided with a variable timer so that the intervals between transfers from enclosure 12 to enclosure 14 and vice versa may be set, as desired by an operator, for the specific test to be performed. It is to be understood that the number of transfers between enclosures 12 and 14 and the time intervals between them are a matter of choice for the operator and selected in accordance with the specific test employed or protocol prescribed or established. A typical test would involve alternate submersions of the workpiece in the cooling expanded mass 25' for 5 minutes. The transfer time, i.e., when the basket 30 is not fully submerged in either basket during a test, may be about 10 seconds.

Since the particles typically used in fluidized bed thermal shock systems are usually electrically non-conductive, the movement of fluidizing gas around the solids sometimes causes a build up of static charges on the bed particles. These charges can impart a charge to the parts being tested.

This invention prevents a build up of these static charges in the fluidized bed of a fluidized bed thermal shock tester or like fluidized bed devices by specific choice of the particulate solid bed media and a suitable electrical grounding arrangement for charge dissipation.

The requirement for the operation of a fluidized bed thermal shock system without build up of static charges is that the charges be dissipated as they form. This dissipation may be accomplished by transferring charge by and between various bed particles to grounded parts of the equipment that are in contact with the bed. The dissipation occurs when the particle strikes the grounded part of the equipment. The materials useful for preparing electrically conducting bed media contemplated by the present invention include all solid materials capable of conducting electricity and being prepared in the required particulate form including metals, metal alloys, carbon, and semi-conducting materials as hereinafter defined.

It has been discovered that electrically conducting bed particles in contact with ground do not build up static charge. This is due to the collision of the particles with the grounded structures in contact with the fluidized bed, e.g. enclosure walls, and/or an electrically grounded support means holding the devices being tested. Any charge on the conducting particles immediately discharge to the walls or the support means.

It has also been demonstrated that the introduction of some electrically conducting particles into a grounded fluidized bed of non-electrically conducting (dielectric) particles reduces or eliminates the static charge buildup in the fluidized bed. For example, 1% by wt. of carbon particles (conducting) added to a grounded fluidized bed of non-conducting particles, e.g. aluminum or zirconium oxide, reduces the static charge buildup. This is due to the dissipation of the static charge from non-conducting particles to conducting particles through particle/particle collision and the conducting particle dissipating the charge to the grounded wall or support means. Since there are non-conducting particles present, the mechanism for dissipation from these particles to the conducting ones involves a slower rate and the net dissipation rate is less than with a bed composed of only conducting particles. Therefore, in some cases, there is some static buildup because the charge formation exceeds the dissipation rate until equilibrium is established, however, this level is significantly below the static charge level for the case of non-conducting particles alone.

It has also been demonstrated that there are what are hereinafter referred to as semi-conducting particles which contain electrically conductive elements in a particular structure. The electrically conductive elements present in these particles may be impurities or specifically added for purposes of the invention. An example of this type of material is Rutile (naturally occurring titanium dioxide) containing 2 to 4% iron oxide in the particle structure. Another example is Aluminum Oxide Abrasive Sand which is 48% Aluminum oxide, 28% Silica dioxide, and 14% Iron oxide (plus 10% miscellaneous metal oxides). The presence of the iron (or other electrically conductive species) in the particle structure increases their ability to discharge static charges and hence they show little or no static charge buildup in grounded fluidized beds. This mechanism is effective despite the fact that these particles exhibit very low electrical conductivity.

Figure 2:
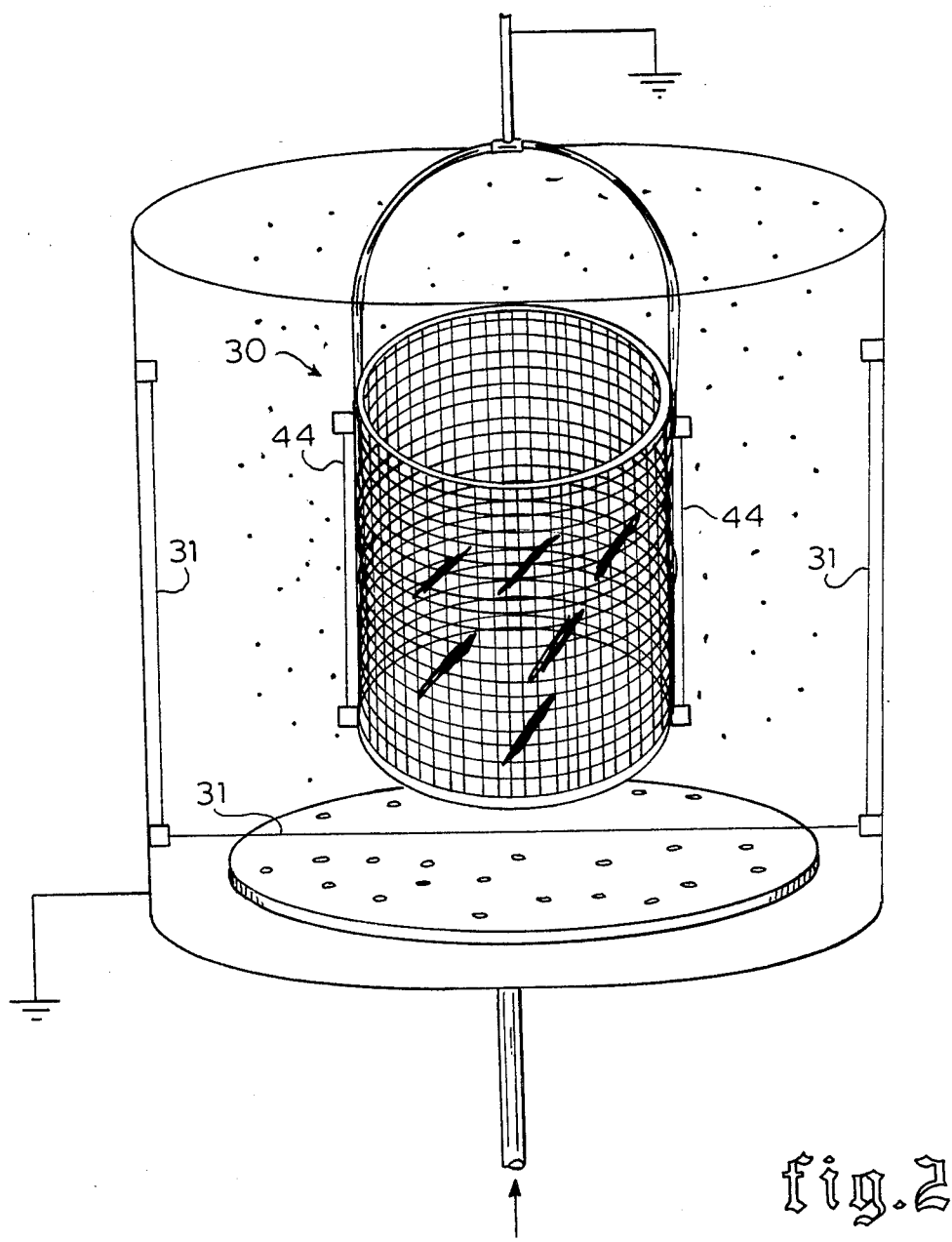
FIG. 2, is a fragmentary isometric view of an alternate embodiment of the present invention.

It has also been demonstrated that increasing the contact area between the grounded wall of the fluid bed enclosures and the fluidized bed of solids and/or increasing the contact area between the grounded fixture holding the devices being tested and the fluidized bed of solids, results in increasing rate of static charge dissipation and a reduced or eliminated static charge level in the fluidized bed. An example of this approach is shown in FIG. 2.

The static charge dissipators 44 are grounded wires with a plurality of cross wires attached thereto forming a high contact area conductor. The fluidized bed flowing through and around the dissipators 44 give up static charges to these structures which in turn dissipate the charges to the grounded fluidized bed enclosure.

While in order to comply with the statutes, the present invention has been described in specific terms, it is to be understood that the invention is not limited to the specific embodiments disclosed herein and that the invention is therefore claimed in any of its forms, modifications or equivalents within the legitimate and valid scope of the claims.

What is claimed is:

1. A fluidized bed device for thermal operations on a workpiece adapted to minimize electrostatic charge comprising:
    at least one enclosure having means for expanding a mass of solid particles therein, said enclosure having a means for supporting a workpiece disposed therein comprising a basket means, having surfaces adapted to allow the passage of fluidized particles to pass therethrough; said surfaces being in electrical communication with an electrical ground;
    a mass of solid particles within the enclosure, at least some of said particles selected from the group consisting of electrically conductive and semi-conductive materials;
    means for contacting the expanded mass with the conductive surfaces; and
    means for controlling the temperature within said enclosure.

2. The fluidized bed device recited in claim 1 wherein:
    the expanded mass contains at least 1% wt. carbon particles.

3. The fluidized bed device recited in claim 1 wherein:
    the expanded mass contains at least some particles selected from the group consisting of metals and metal alloys.

4. The fluidized bed device recited in claim 1 wherein:
    the expanded mass contains at least some aluminum oxide sand particles.

5. The fluidized bed device recited in claim 1 wherein:
    the expanded mass contains at least some Rutile particles.

6. The fluidized bed device recited in any one of claims 1, 2, 3 or 4 wherein:
    the means for contacting the expanded mass with electrical ground comprises a plurality of grounded electrically conductive wires disposed within the enclosure so that they contact the expanded mass.

7. The fluidized bed device recited in claim 1 wherein a semiconductor device is disposed in the means for supporting a workpiece.

8. The fluidized bed device recited in claim 1 further comprising at least one dissipator mounted on the means for supporting a workpiece in order to dissipate static charges in the vicinity of the workpiece.

9. The fluidized bed device recited in claim 8 wherein the surfaces of the enclosure consist of electrically conductive surfaces.

10. The fluidized bed device recited in claim 9 wherein the particles consist of electrically conductive particles.

11. The fluidized bed device recited in claim 1 wherein:
    the expanded mass contains at least some particles selected from the group consisting of titanium dioxide and titanium oxide with solute additions in particulate form of other metal oxide phases selected from the group consisting of ferrites, chromia, and alumina.

12. A device for thermal testing, which comprises:
    a first and second enclosure each having means for producing an expanded mass of solid particles therein including at least some particles selected from the group consisting of conductive and semi-conductive materials;
    support means for supporting a workplace within said enclosures;
    means for adjusting the temperature in each enclosure;
    means for contacting the expanded mass in each enclosure with electrical ground; and electromechanical means for transporting the support means between the first and second enclosure.

13. A device for thermal testing as recited in claim 12 wherein:
    the support means comprises an electrically conductive wire basket in communication with electrical ground having at least one dissipator affixed thereto for increasing the surface area in which particles may dissipate electrostatic build-up.

14. A fluidized bed device, which comprises:

at least one enclosure having means for producing an expanded mass of solid particles therein including at least some particles selected from the group consisting of conductive and semi-conductive materials;

means for contacting the expanded mass with electrical ground; and means for controlling the temperature within said enclosure, wherein an electrically conductive means for supporting a workpiece comprises a wire basket comprising a plurality of intermeshed wires surrounding a workpiece, adapted to allow the passage of fluidized particles to pass therethrough; further comprising a plurality of dissipators mounted on the means for supporting a workpiece in order to dissipate static charges in the vicinity of the workpiece and a plurality of dissipators mounted within the enclosure in electrical communication with the walls of the enclosure.

15. A method of thermal testing semiconductor devices comprising:

providing a fluidized bed of solid particulate matter;

placing the semiconductor devices in an electrically conductive workpiece holder which is disposed within the fluidized bed;

contacting the semiconductor devices with particles of the fluidized bed wherein at least some of the particles are electrically conductive materials;

dissipating electrostatic charge from the particles by contacting the particles with grounded conductive surface, wherein the surfaces comprise electrically conductive, grounded walls of the fluidized bed, electrically conductive, grounded, charge dissipating wires disposed in the fluidized bed, and the workpiece holder.

* * * * *